United States Patent

Prasad et al.

Patent Number: 5,462,437
Date of Patent: * Oct. 31, 1995

[54] DENTAL ALLOYS FOR COMPOSITE AND PORCELAIN OVERLAYS

[75] Inventors: Arun Prasad, Cheshire; Martin Schulman, Orange, both of Conn.

[73] Assignee: Jeneric/Pentron Incorporated, Wallingford, Conn.

[*] Notice: The portion of the term of this patent subsequent to Jun. 13, 2012, has been disclaimed.

[21] Appl. No.: 149,960

[22] Filed: Nov. 10, 1993

[51] Int. Cl.$^6$ .................................................. A61C 13/08
[52] U.S. Cl. .................. 433/207; 433/200.1; 420/505; 420/508; 420/509; 420/510; 420/511; 420/580; 420/589; 148/430; 148/442
[58] Field of Search ........................ 420/508, 509, 420/510, 511, 580, 425, 426, 427, 505, 512, 589, 503; 148/430, 442; 433/200.1, 207

[56] References Cited

U.S. PATENT DOCUMENTS

| | | | |
|---|---|---|---|
| 3,981,723 | 9/1976 | Tuccillo | 420/508 |
| 4,201,577 | 5/1980 | Ingersoll et al. | 420/508 |
| 4,297,266 | 10/1981 | Ibsen et al. | 260/42.14 |
| 4,604,366 | 8/1986 | Kacicz et al. | 501/6 |
| 4,804,517 | 2/1989 | Schaffer et al. | 420/587 |
| 5,221,207 | 6/1993 | Schoeck et al. | 420/509 X |
| 5,276,068 | 1/1994 | Waknine | 522/28 |

FOREIGN PATENT DOCUMENTS 61-60852  3/1986  Japan.

Primary Examiner—W. Gary Jones
Assistant Examiner—Sean Vincent
Attorney, Agent, or Firm—Watson, Cole, Grindle & Watson

[57] ABSTRACT

A dental alloy is provided which is compatible with a wide variety of composites and porcelain compositions. The alloy has a melting range of between about 870° C. and 1230° C. and a coefficient of thermal expansion of between $15.5 \times 10^{-6}$ and $17.5 \times 10^{-6}$ in/in/° C. when heated from room temperature to 500° C. The alloy contains between one and 85 percent by weight gold, between two and 65 percent by weight of a thermal expansion adjuster, between 0.25 and 34 percent by weight of a strengthener and oxide former, up to about one percent by weight grain refiner, and up to about 0.25 percent by weight deoxidizer.

19 Claims, No Drawings

DENTAL ALLOYS FOR COMPOSITE AND PORCELAIN OVERLAYS

FIELD OF THE INVENTION

The present invention relates to dental alloys which can be cast or machined as a full crown, bridge, inlay or onlay or as a substructure to accept an overlay of a suitable composite or porcelain composition.

BACKGROUND OF THE INVENTION

Dental copings or posts coated with a dental porcelain have been used in restorations of single or multiple teeth. The jacket or covering of dental porcelain on the metal coping or post provides a restoration which closely resembles a natural tooth. Dental crown and bridge restorations are often made with a metal base comprising a malleable metal alloy which is gentle on opposing dentition. Such restorations are well known and have been used for many years.

The general technique for the construction of a porcelain coated dental restoration involves first taking an impression of a denture area that has been prepared to receive the restoration. A die is prepared from the impression, and a metal base ("coping" or "post") is cast to fit this die. The metal base has an internal shape to match the prepared denture. A porcelain powder is then mixed with water to form a slurry which is then applied to the metal base, or a portion of a metal base, by standard procedures. The slurry is shaped in the form of the finished tooth, crown, multiple unit bridge, inlay or onlay. The porcelain is then dried, and fired in a furnace at a desired firing temperature. The restoration may be fired several times before the final form is obtained, and the porcelain may be applied in several layers. Alternatively, a resin based composite may be used in layers to form the outer coatings of the restoration.

To form a strong bond between a dental porcelain and a dental alloy, it has been determined that the temperature range in which the glass-forming components of a porcelain composition melt and mature should be within about 150° C. below the melting point of the dental alloy. Herein, the temperature or temperature range in which the glass-forming particles in the porcelain mixture melt to form a glass melt is referred to as the fusion temperature or the fusion temperature range. To form a strong bond, it is also important that the thermal expansion coefficient of the porcelain be close to, but slightly less than, that of the dental alloy.

There is a significant temperature change when heating a restoration from room temperature to the firing temperature, as occurs when a restoration is alternately fired and cooled. Therefore, significant stress can be induced in the restoration if the thermal expansion of the porcelain coating does not closely match that of the dental alloy base.

Dental alloy bases that are most often employed today in such restorations include gold, high and low gold alloys including goldpalladium alloys, silver-palladium alloys, high palladium alloys, nickel-chrome-molybdenumtype alloys, gold-silver-palladiumalloys and palladium-copper alloys. Gold and its alloys are preferred metals for a metal base due to their biocompatibility with the human body. Precious metal and alloys exhibit thermal expansion coefficients of about $13.6 \times 10^{-6}$ to $18.3 \times 10^{-6}$ in/in/° C. and thus ceramics which are used with gold metal and alloys should have similarly high thermal expansion coefficients.

Crown and bridge alloys have different properties when compared to traditional ceramic alloys used with a fused porcelain veneer. Crown and bridge alloys have a lower casting temperature and thus a higher coefficient of thermal expansion than traditional ceramic alloys. Traditional porcelains would encounter fracturing problems when baked onto the crown and bridge alloys due to the large difference in thermal expansion coefficients of the alloys and the porcelains.

Table I below shows the melting or fusion temperature range of traditional ceramic alloys, traditional dental porcelains and crown and bridge alloys.

TABLE I

| | MELTING/FUSION TEMP. RANGE (°C.) | COEF. of THERM. EXP. (in/in/°C.) (RT –500° C.) |
|---|---|---|
| CERAMIC ALLOYS | 1050–1300 | $13.6–15 \times 10^{-6}$ |
| TRADITIONAL PORCELAIN | 925–1000 | $12.7–14 \times 10^{-6}$ |
| CROWN AND BRIDGE ALLOYS | 815–1000 | $15.5–18.3 \times 10^{-6}$ |

It is desirable to provide a family of dental alloys which can be used with a wide variety of dental porcelains and composites.

SUMMARY OF THE INVENTION

It is an object of the present invention to provide a dental alloy specifically formulated to be compatible with a wide variety of composites and porcelain compositions. More particularly, it is an object of the present invention to provide a dental alloy having a coefficient of thermal expansion when heated from room temperature to 500° C. of between $15.5 \times 10^{-6}$ and $17.5 \times 10^{-6}$ in/in/° C.

It is also an object of the present invention to provide a dental alloy which has a melting range of between about 870° C. and 1230° C.

According to one embodiment of the present invention, a dental alloy is provided which has both a melting range of from 870° C. and 1230° C. and a coefficient of thermal expansion which is between $15.5 \times 10^{-6}$ and $17.5 \times 10^{-6}$ in/in/° C. when heated from room temperature to 500° C.

It is further an object of the present invention to provide a dental alloy which has a minimum yield strength value of 40,000 psi and a minimum elongation value of two percent.

The present invention also encompasses alloys which would traditionally be classified as crown and bridge alloys, but which can be coated with porcelain compositions and resin-based composites to form more complicated, natural-looking dental restorations. Crown and bridge alloys, by definition, have been used to make dental restorations which are not coated with porcelains. However, according to an embodiment of the present invention, alloys of this type are provided which are capable of being coated with a porcelain or composite. Herein, the alloys of the present invention will be referred to as dental alloys, and include alloys which would traditionally be thought of as crown and bridge alloys.

According to one embodiment, the alloys of the present invention can be cast to include full cast crowns and substructures which can be entirely or partially coated with a dental porcelain or composite to form a desired restoration. It may be desired to coat only a portion of a multiple unit bridge.

The above and other objects may be achieved according to the present invention by providing a dental alloy which comprises between one and 85 percent by weight gold, between two and 65 percent by weight of a thermal expansion adjuster, between 0.25 and 34 percent by weight of a strengthener and oxide former, up to about three percent by weight grain refiner, and up to about 0.25 percent by weight deoxidizer.

The thermal expansion adjuster preferably is at least one member selected form the group consisting of platinum, palladium and silver. The strengthener and oxide former preferably comprises at least one member selected from the group consisting of copper, tin, indium, manganese, zinc, chromium, titanium, tantalum, gallium, germanium and iron. The grain refiner preferably comprises at least one member selected from the group consisting of iridium, ruthenium, rhenium, rhodium and cobalt. The deoxidizer comprises at least one member selected from the group consisting of calcium, boron, silicon, aluminum, lithium and phosphorus.

The invention may be more fully understood with reference to the detailed description which follows. The invention is not limited to the exemplary embodiments but should be recognized as contemplating all modifications within the skill of an ordinary artisan.

DETAILED DESCRIPTION OF THE INVENTION

The dental alloys according to the present invention are formulated to have a coefficient of thermal expansion which is between $15.5 \times 10^{-6}$ and $17.5 \times 10^{-6}$ in/in/° C. when heated from room temperature to 500° C., and a melting temperature of between 870° C. and 1230° C. The alloys of the present invention are particularly well suited for being coated with a wide variety of composites and porcelain compositions. Preferably, the alloy exhibits a yellow color.

The present invention provides a dental alloy which comprises between one and 85 percent by weight gold, between two and 65 percent by weight of a thermal expansion adjuster, between 0.25 and 34 percent by weight of a strengthener and oxide former, up to about three percent by weight grain refiner, and up to about 0.25 percent by weight deoxidizer.

The dental alloys according to the present invention comprise between one and 85 percent by weight gold. According to the present invention, alloys comprising between about two and 75 percent by weight gold are preferred while those having between about two and 60 percent by weight are even more preferred. The gold provides a desirable yellow coloration to the restoration base. Also, gold is preferred in dental alloys because it is highly biocompatible with the human body.

The thermal expansion adjuster is preferably at least one member selected form the group consisting of platinum, palladium and silver. Generally, the property of thermal expansion is inversely related to the melting point or range of an alloy. Platinum and palladium raise the melting point or range when added to gold alloys. Likewise, platinum and palladium may be added to lower the coefficient of thermal expansion of the alloy. Silver may be added to lower the melting point or range of a gold alloy and likewise raise thermal expansion properties of the alloy.

The addition of platinum, palladium or silver dilutes the yellow color of the gold without substantial loss of resistance to corrosion and tarnish.

Combinations of platinum, palladium and silver may be used to provide a gold alloy having a specific coefficient of thermal expansion. The choice of thermal expansion adjusters and the amount of each to use is largely dependent on whether the alloy is to be used as a metal substructure requiring porcelain or composite overlays or as a full cast crown and bridge alloy.

The selection of an element or combination of elements from this group may also be dependent on the thermal expansion coefficient of the overlay material. The thermal expansion of the alloy is adjusted to be slightly greater than the thermal expansion of the overlay material. Matching the thermal expansions in this manner enables the formation of compressive stress at the interface between the alloy and the overlay material. Achieving this condition strengthens the overlay material which is generally weaker than the alloy substrate.

Alloys consisting of gold and at least one of platinum, palladium and silver are relatively weak and can be used only in low stress-bearing areas. In order to extend the application of such alloys to a use in areas of high masticatory stress, they must further be strengthened. A strengthener and oxide former may be used for this purpose.

The strengtheners and oxide formers used in the alloys of the present invention preferably comprise at least one member selected from the group consisting of tin, indium, manganese, chromium, titanium, tantalum, zinc, gallium, germanium, iron and copper. These elements not only strengthen the alloy but also allow the formation of adherent oxides, which are responsible for the chemical bonding of porcelains and composite coatings to the alloy.

These strengthening elements also contribute to the control of the melting point or range of the alloy as well as thermal expansion properties. The amount of strengthening elements for use in alloys to which a dental porcelain will be fused is dictated by the fusion range of the porcelain. If the porcelain is a lower fusing porcelain, higher amounts of these elements can be used without causing the alloy to become too brittle.

Of the identified strengtheners and oxide formers, tin and indium are preferred with tin being more preferred.

Grain refiners are added to the alloy to control grain size by providing nucleating sites as the alloy melt solidifies. The smaller the grain size, the better the formability of the alloy and the greater the number of grains over the thickness of alloy. Smaller grain sizes also improve the ability of the alloy to be polished once cast, and improves resistance to both corrosion and tarnishing. Smaller grain sizes also make the alloy less vulnerable to heat tears or cracks during casting of thin wall copings. Smaller grain size in an alloy additionally enables the edges and margins of the casting to be non-ragged and easily burnished. A margin is defined herein as the area where the dental coping comes in contact with the gum-tissue.

According to the present invention, the grain refiner preferably comprises at least one member selected from the group consisting of iridium, ruthenium, rhenium, cobalt and rhodium. Preferably, grain refiner is added in an amount sufficient to control grain size and to improve the formability, polishibility and corrosion and tarnish resistance. Up to about 0.1 percent by weight is usually sufficient, however, greater amounts may be used.

Of the identified grain refiners, iridium is preferred when the alloy is gold based. Ruthenium and rhenium are more preferred when the alloy has higher amounts of platinum, palladium and silver. Rhodium is less preferred because of its high cost.

Deoxidizers are added to alloys to prevent the loss of important ingredients of the alloy during heating and melting operations. Deoxidizers prevent such loss by sacrificing themselves. They also act as scavengers to rid the melt of gaseous inclusions. Although the present invention is not limited to alloys which contain a deoxidizer, without the addition of an oxidizer bubbling may develop during the porcelain firing cycle.

According to the present invention, the deoxidizer comprises at least one member selected from the group consisting of calcium, boron, silicon, aluminum, lithium and phosphorus. Of these, calcium and boron are preferred. Preferably, the deoxidizer is present in an amount sufficient to substantially prevent the oxidation of other metals in the alloy during alloy melting.

Calcium is a very potent deoxidizer and is likewise very reactive. Unfortunately, elemental calcium is difficult to handle because it so readily reacts with humidity in the air and oxidizes. Boron may be used in combination with calcium to minimize oxidation of the calcium. For example, $CaB_6$ is a preferred deoxidizer in the alloys of the present invention.

Table II below shows a number of examples of alloys made in accordance with the present invention.

TABLE II

| Component | EXAMPLE NO. | | | | |
|---|---|---|---|---|---|
| | I | II | III | IV | V |
| Au | 2 | 40 | 60 | 74 | 82 |
| Pt | — | 2.0 | 5 | 9 | 6 |
| Pd | 40 | 20 | 7.5 | — | 5 |
| Ag | 24.9 | 24.9 | 23.4 | 8.9 | 5.9 |
| Cu | — | — | — | 5 | — |
| In | 29 | 10 | 4 | 1 | 1 |
| Mn | — | — | — | 1 | — |
| Zn | 4 | 3 | — | 1 | — |
| Ir | — | 0.05 | 0.05 | 0.05 | 0.05 |
| Ru | 0.05 | — | — | — | — |
| $CaB_6$ | 0.05 | 0.05 | 0.05 | 0.05 | 0.05 |

Examples I–V exhibit coefficient of thermal expansion values between 15.5 and $17.5 \times 10^{-6}$ in/in/° C. Their melting ranges lie between 870° C. and 1230° C. The yield strength values vary between 40,000 psi and 100,000 psi and the elongation values fall between two percent and 25 percent.

What follows is a description of some exemplary porcelains which may be used to coat the alloys of the present invention. The present invention is not limited to restorations comprising the described porcelains.

A wide variety of porcelain mixtures form desirable porcelain coatings when fused to dental alloys. Different mixtures are preferred for the different layers of the restoration. The restoration may comprise a bond layer, an opaque porcelain layer, a body layer and an incisal.

Differences in the components used for each layer and differences in the amounts of the components enable the different layers to exhibit different optical and thermal properties.

A preferred porcelain will have a fusion range of 725° C. to 850° C. and a coefficient of thermal expansion between $15.0 \times 10^{-6}$ to $17.0 \times 10^{-6}$ in/in/° C. when heated from 25° to 500° C. The dental porcelain may comprise oxides of Si, Al, K, Na, Li, Ca, Mg, Zr, Sn, Ti, Y, Ce and Eu. Some preferred porcelain compositions contain at least 33 percent by weight leucite. Preferred porcelains may also contain various pigments for coloration and hydroxyl and fluoride groups in their glass network.

A wide variety of composites can also be used and include those made of glass fillers and resins such as Bis-GMA, TEGDMA, UDMA and PCDMA. The composites may be cured by means such as photo-initiation, chemical curing, combinations of photo-initiation and chemical curing, and heat curing. The curing may also be cured under water, under vacuum and under pressure of inert gases. One such composite is available as Conquest® from Jeneric/Pentron Inc., Wallingford, Conn.

Although the present invention has been described in connection with preferred embodiments, it will be appreciated by those of skill in the art that additions, modifications, substitutions and deletions not specifically described may be made without departing from the spirit and scope of the invention defined in the appended claims.

We claim:

1. A dental alloy which can be coated with a composite or a porcelain composition to form a dental restoration, said alloy comprising:

(A) between one and 60 percent by weight gold;

(A1) between 23.4 and 24.9 percent by weight silver;

(B) up to 41.6 percent by weight thermal expansion adjuster comprising at least one member selected from the group consisting of platinum and palladium;

(C) between 0.25 and 34 percent by weight strengthener and oxide former comprising at least one member selected from the group consisting of tin and indium;

(D) up to about three percent by weight grain refiner comprising at least one member selected from the group consisting of iridium, ruthenium, rhenium, cobalt and rhodium; and (E) up to about 0.25 percent by weight deoxidizer comprising at least one member selected from the group consisting of calcium, boron, silicon, aluminum, lithium and phosphorus, said alloy having a yellow color, a melting range of between 870° C. and 1230° C., and a coefficient of thermal expansion between $15.5 \times 10^{-6}$ and $17.5 \times 10^{-6}$ in/in/° C. when heated from room temperature to 500° C.

2. A dental alloy as defined in claim 1, wherein component (D) is present in an amount of up to about one percent by weight.

3. A dental alloy as defined in claim 1, wherein component (D) comprises iridium present in an amount of up to about one percent by weight.

4. A dental alloy as defined in claim 1, wherein component (D) comprises at least one member selected from the group consisting of ruthenium and rhenium present in an amount of up to about one percent by weight.

5. A dental alloy as defined in claim 1, wherein component (E) comprises at least one member selected from the group consisting of calcium and boron and is present in an amount of up to about 0.25 percent by weight.

6. A dental alloy as defined in claim 1, wherein said alloy exhibits a yellow color.

7. A dental restoration comprising a dental alloy coated with a dental porcelain composition, wherein said dental alloy comprises:

(A) between one and 60 percent by weight gold;

(A1) between 23.4 and 24.9 percent by weight silver;

(B) up to 41.6 percent by weight thermal expansion adjuster comprising at least one member selected from the group consisting of platinum and palladium;

(C) between 0.25 and 34 percent by weight strengthener and oxide former comprising at least one member selected from the group consisting of tin and indium;

(D) up to about three percent by weight grain refiner comprising at least one member selected from the group consisting of iridium, ruthenium, rhenium, cobalt and rhodium; and (E) up to about 0.25 percent by weight deoxidizer comprising at least one member selected from the group consisting of calcium, boron, silicon, aluminum, lithium and phosphorus, said alloy having a yellow color, a melting range of between 870° C. and 1230° C., and a coefficient of thermal expansion between $15.5\times10^{-6}$ and $17.5\times10^{-6}$ in/in/° C. when heated from room temperature to 500° C.

8. A dental restoration alloy as defined in claim 7, wherein said alloy exhibits a yellow color.

9. A dental restoration alloy as defined in claim 7, wherein said porcelain comprises at least 33 percent by weight $K_2O \cdot Al_2O_3, 1 \cdot 4SiO_2$.

10. A dental restoration comprising a dental alloy coated with a dental composite, wherein said dental alloy comprises:

(A) between one and 60 percent by weight gold;

(A1) between 23.4 and 24.9 percent by weight silver;

(B) up to 41.6 percent by weight thermal expansion adjuster comprising at least one member selected from the group consisting of platinum and palladium;

(C) between 0.25 and 34 percent by weight strengthener and oxide former comprising at least one member selected from the group consisting of tin and indium;

(D) up to about three percent by weight grain refiner comprising at least one member selected from the group consisting of iridium, ruthenium, rhenium, cobalt and rhodium; and (E) up to about 0.25 percent by weight deoxidizer comprising at least one member selected from the group consisting of calcium, boron, silicon, aluminum, lithium and phosphorus, said alloy having a yellow color, a melting range of between 870° C. and 1230° C., and a coefficient of thermal expansion between $15.5\times10^{-6}$ and $17.5\times10^{-6}$ in/in/° C. when heated from room temperature to 500° C.

11. A dental restoration as defined in claim 10, wherein said alloy exhibits a yellow color.

12. A dental restoration as defined in claim 10, wherein said dental composite comprises a resin selected from a group of Bis-GMA, TEGDMA, UDMA and PCDMA.

13. A dental restoration as defined in claim 12, wherein said dental composite comprises polycarbonate dimethacrylate.

14. A dental alloy which can be coated with a composite or a porcelain composition to form a dental restoration, said alloy comprising:

(A) between 60 and 85 percent by weight gold;

(B) between 5.9 and 23.4 percent by weight silver;

(C) between 9 and 12.5 percent by weight thermal expansion adjuster comprising at least one member selected from the group consisting of platinum and palladium including between 5 and 7.5 percent by weight palladium, wherein the combined weight of all platinum and palladium in said alloy is between 9 and 12.5 percent by weight based on the weight of said alloy;

(D) between 0.25 and 34 percent by weight strengthener and oxide former comprising at least one member selected from the group consisting of copper, tin, indium, manganese, zinc, chromium, titanium, tantalum, gallium, germanium and iron;

(E) up to about three percent by weight grain refiner comprising at least one member selected from the group consisting of iridium, ruthenium, rhenium, cobalt and rhodium; and (F) up to about 0.25 percent by weight deoxidizer comprising at least one member selected from the group consisting of calcium, boron, silicon, aluminum, lithium and phosphorus, said alloy having a yellow color, a melting range of between 870° C. and 1230° C., and a coefficient of thermal expansion between $15.5\times10^{-6}$ and $17.5\times10^{-6}$ in/in/° C. when heated from room temperature to 500° C.

15. A dental alloy as defined in claim 14, wherein said alloy is comprised of between 1 and 4 percent by weight indium.

16. A dental alloy as defined in claim 14, wherein said alloy contains $CaB_6$ present in an amount of up to 0.25 percent by weight.

17. A dental restoration comprising a dental alloy coated with a dental composition wherein said composition comprises one member selected from group consisting of dental composites and dental porcelain compositions, and wherein said dental alloy comprises:

(A) between 60 and 85 percent by weight gold;

(B) between 5.9 and 23.4 percent by weight silver;

(C) between 9 and 12.5 percent by weight thermal expansion adjuster comprising at least one member selected from the group consisting of platinum and palladium including between 5 and 7.5 percent by weight palladium, wherein the combined weight of all platinum and palladium in said alloy is between 9 and 12.5 percent by weight based on the weight of said alloy;

(D) between 0.25 and 34 percent by weight strengthener and oxide former comprising at least one member selected from the group consisting of copper, tin, indium, manganese, zinc, chromium, titanium, tantalum, gallium, germanium and iron;

(E) up to about three percent by weight grain refiner comprising at least one member selected from the group consisting of iridium, ruthenium, rhenium, cobalt and rhodium; and (F) up to about 0.25 percent by weight deoxidizer comprising at least one member selected from the group consisting of calcium, boron, silicon, aluminum, lithium and phosphorus, said alloy having a yellow color, a melting range of between 870° C. and 1230° C., and a coefficient of thermal expansion between $15.5\times10^{-6}$ and $17.5\times10^{-6}$ in/in/° C. when heated from room temperature to 500° C.

18. A dental restoration comprising a dental alloy coated with a dental composition wherein said composition comprises one member selected from the group consisting of dental composites and dental porcelain compositions, and wherein said dental alloy comprises:

(A) between 60 and 85 percent by weight gold;

(B) between 5.9 and 23.4 percent by weight silver;

(C) between 9 and 12.5 percent by weight thermal expansion adjuster comprising at least one member selected from the group consisting of platinum and palladium wherein the combined weight of all platinum and palladium in said alloy is between 9 and 12.5 percent by weight based on the weight of said alloy;

(D) between 0.25 and 34 percent by weight tin;

(E) up to about three percent by weight grain refiner comprising at least one member selected from the group consisting of iridium, ruthenium, rhenium, cobalt and rhodium; and (F) up to about 0.25 percent by weight deoxidizer comprising at least one member selected from the group consisting of calcium, boron, silicon, aluminum, lithium and phosphorus, said alloy having a yellow color, a melting range of between 870° C. and 1230° C., and a coefficient of thermal expansion between $15.5 \times 10^{-6}$ and $17.5 \times 10^{-6}$ in/in/° C. when heated from room temperature to 500° C.

19. A dental restoration as defined in claim 18, wherein said alloy is comprised of between 5 and 7.5 percent by weight palladium.

* * * * *